(12) United States Patent
Kurtz et al.

(10) Patent No.: US 6,267,011 B1
(45) Date of Patent: Jul. 31, 2001

(54) METHOD AND APPARATUS FOR DETERMINING THE TRUE STRESS AND TRUE STRAIN BEHAVIOR OF A DUCTILE POLYMER

(75) Inventors: Steven Michael Kurtz, Haddonfield, NJ (US); Charles William Jewett, San Jose; Jude Reynold Foulds, Los Altos, both of CA (US)

(73) Assignee: Exponent, Inc., Menlo Park, CA (US)

( * ) Notice: Subject to any disclaimer, the term of this patent is extended or adjusted under 35 U.S.C. 154(b) by 0 days.

(21) Appl. No.: 09/281,786

(22) Filed: Mar. 31, 1999

(51) Int. Cl.$^7$ ................................ G01D 1/16; G01D 7/02

(52) U.S. Cl. .................................................. 73/789

(58) Field of Search ........................... 73/789, 788, 760, 73/863, 95, 88 F, 724; 428/500, 480

(56) References Cited

U.S. PATENT DOCUMENTS

| | | |
|---|---|---|
| 1,237,051 | 8/1917 | Kammerer . |
| 2,262,084 | 11/1941 | Alexander . |
| 4,062,994 * | 12/1977 | Millman et al. ..................... 428/101 |
| 4,432,239 | 2/1984 | Bykov . |
| 4,567,774 | 2/1986 | Manahan et al. . |
| 4,667,095 | 5/1987 | Hatanaka et al. . |
| 5,165,287 | 11/1992 | Manahan, Sr. . |
| 5,184,517 | 2/1993 | Kelzer . |
| 5,458,002 * | 10/1995 | Millman et al. ....................... 73/789 |
| 5,507,189 | 4/1996 | Kim et al. . |
| 5,568,259 | 10/1996 | Kamegawa . |
| 5,757,473 | 5/1998 | Kanduth et al. . |

OTHER PUBLICATIONS

Bayoumi:, M. R. "Study of the Relationship Between Fracture Toughness and Budge Ductility", Int. Journ. of Fracture 23(1983), p. 71–79.

Chakrabarty, J. "A Theory of Stretch Forming Over Hemispherical Punch Heads", Int. J. Mech. Sc: vol. 12(1970) p. 315–325.

Cheon et al. "Initial Deformation During Small Punch Testing", J TEVA vol. 24, No. 4, Jul. 1996, p. 255–262.

Edidin et al "Degradation of Through–Thickness Mechanical Properties OverTime is More Secure than Previously Estimated Using Indirect Measurement Techniques", 45$^{th}$ Annual Meeting, Orthopaedic Research Society, Feb. 1–4, 1999, p. 74.

Edidin et al "Direct Correlation of Abrasive Wear for Irradiation–Crosslinked UHMWPE with Large–Deformation Mechanical Behavior Determined at the Articulating Surface", 45$^{th}$ Annual Meeting, Orthopaedic Research Society, Feb. 1–4, 1999, p. 101.

Edidin et al. "Direct Correlation of Abrasive Wear Resistance of Irradiation–Crosslinked UHMWPE Cups with Large Deformation Mechanical Behavior Determined at the Articulated Surface", 24$^{th}$ Annual Meeting of the Society for Biomaterials, vol. XXI, Apr. 22–26, 1998, p. 220.

Edidin et al. "Measurement of Average Wear Rates of Four Clinically Applied Polymeric Materials in a Modern Validated Hip Simulator,", 45$^{th}$ Annual Meeting, Orthopaedic Research Society, Feb, 1–4, 1999, p. 856.

(List continued on next page.)

Primary Examiner—Benjamin R. Fuller
Assistant Examiner—Octavia Davis
(74) Attorney, Agent, or Firm—Hall, Priddy, Myers & Vande Sande

(57) ABSTRACT

A small punch test apparatus is used to determine true stress and true strain in a ductile polymeric material as it undergoes deformation by the punch head. The information gathered can be used comparatively to assess the acceptability of a body implant subjected to sterilization against similar information obtained on another implant of the same polymer already known to be acceptable.

24 Claims, 6 Drawing Sheets

OTHER PUBLICATIONS

Edidin et al. "Plasticity Induced Damage Layer is a Precursor to Wear in Radiation–Crosslinked UHMWPE Acetabular Components for Total Hip Replacement", J. Arthroplasty (1998), In Review.

Foulds et al. "Fracture Toughness by Small Punch Testing", JTEVA, vol. 23, No. 1, Jan. 1995, p. 3–10.

Ghosh et al. "Failure in Thin Sheets Stretched Over Rigid Punches", Metallurgical Transactions A, vol. 6A, May 1975, p. 1065–1074.

Ghosh et al. "Strain Hardening and Instability in Biaxially Stretched Sheets", Metallurgical Transactions A, vol. 4, Apr. 1973, p. 1113–1123.

Hoffman et al. "Elastic and Plastic Behavior of Submicrometer–Sized Polycrystalline NiAl", Acta Materials, (1996) vol. 44, No. 7, p. 2729–2736.

Hoffman et al. "Quantitative Measurements of Young's Modulus Using the Miniaturized Disk–Bend Test", Materials Science and Engineering A202, (1995) p. 18–25.

Joo et al. "The Use of Small Punch (Bulge) Tests to Estimate Fracture Stress in the Lower Shelf Regime", JTEVA, vol. 20, No. 5, Sep. 1992, p. 336–342.

Keeler et al. "Plastic Instability and Fracture in Sheets Stretched Over Rigid Punches", Transactions of American Society for Metals, vol. LVI, Mar.–Jun.–Sep. Dec. 1963, p. 25–48.

Kurtz et al. "Effect of Crosslinking on Abrasive Wear Resistance, Crystalline Morphology, and the Large–Deformation Mechanical Behavior at the Articulating Surface", Abstracts of the Third World Congress of Biomechanics, Aug. 2–8, 1998, p. 349(a).

Kurtz et al. "Mechanical Characterization of Ultra–High Molecular Weight Polyethylene Using the Small Punch Test After Gamma Sterilization and Aging", Transactions $24^{th}$ Annual Meeting of the Society for Biomaterials, vol. XXI, Apr. 22–26, 1998, p. 500.

Kurtz et al. "A Miniature–Specimen Mechanical Testing Technique Scaled to the Articulating Surface of Polyethylene Components for Total Joint Arthroplasty", $10^{th}$ Annual Symposium of the International Society for Technology in Arthroplasty, Sep. 25–27, 1997, p. 66–67.

Kurtz et al. "Miniature Specimen Mechanical Testing Technique Scaled to Articulating Surface of Polyethylene Components for Total Joint Arthroplasty", J. Biomed Mater Res (Appl Biometer) 43:000–000, 1998, p. 1–7.

Kurtz et al. "Radiation and Chemical Crosslinking Promote Strain Hardening Behavior and Molecular Alignment in Ultra–High Molecular Weight Polythylene During Multi–Axial Loading Conditions", Submitted: Jan. 12, 1999, p. 1–25.

Kurtz et al. "Radiation and Peroxide Crosslinking Promotes Strain Hardening Behavior and Molecular Alignment in UHMWPE Under Multiaxial Loading Conditions", $45^{th}$ Annual Meeting, Orthopaedic Research Society, Feb. 1–4, 1999, p. 842.

Kurtz et al. "Small Punch Test for Characterization of Aged UHMWPE After Gamma–Sterilization in Air and Nitrogen", Transaction of the $44^{th}$ Annual Meeting, Orthopaedic Reseach Society, Mar. 16–19 (1998), p. 361.

Kurtz et al. "Small Punch Testing for Characterization of Ultra–High Molecular Weight Polyethylene Used in Total Joint Replacements", 1997 Advances in Bioengineering, BED–vol. 36, p. 307–308.

Kurtz et al. "Technological Advancement in the Sterilization, Processing, and Crosslinking of UHMWPE for Total Joint Replacements", Biomaterials (1998) In Review.

Kurtz et al. "Ultimate Properties and Crystalline Morphology of Ultra–High Molecular Weight Polyethylene During Uniaxial and Biaxial Tension", $24^{th}$ Annual Meeting of the Society for Biomaterials, Apr. 22–26, 1998, p. 125.

Kurtz et al. "Validation of a Small Punch Testing Technique to Characterize the Mechanical Behavior of Ultra–High–Molecular–Weight Polyethylene", Biomaterials, vol. 18, No. 24 (1997), p. 1659–1663.

Levine et al. "Mechanical Behavior of UHMWPE Characterized by Uniaxial and Biaxial Tension Tests", $45^{th}$ Annual Meeting, Orthopaedic Research Society, Feb. 1–4, 1999, p. 820.

Li et al. "A Simple, Versatile Miniaturized Disk–Bend Test Apparatus for Quantitative Yield–Stress Measurements", Metallurgical Transactions A, vol. 22a, Sep. 1991, p. 2061–2068.

Mao et al. "Small Punch Test to Predict Ductile Fracture Toughness $J_{ic}$ and Brittle Fracture Toughness $K_{ic}$", Scripta Metallurgica et Materiaia, vol. 25, p. 2481–2485.

Mao et al. "Characterization of Fracture Behavior in Small Punch Test by Combined Recrystallization–Etch Method and Rigid Plastic Analysis", JTEVA, vol. 15, No. 1, 1987, p. 30–37.

Mao et al. "Development of a Further Miniaturized Specimen of 3mm Diameter For Tem Disc (0 3mm) Small Punch Tests", Journal of Nuclear Materials, 150 (1987) p. 42–52.

Meyers et al. "Optimization of Test Parameters for Quantitative Stress Measurements Using the Miniaturized Disk–Bend Test", JTEVA, vol. 21, No. 4, Jul. 1993, p. 263–271.

Omat et al. "The Load Carrying Capacity of Circular Plates at Large Deflection", Journal of Applied Mechanics, vol. 23, No. 1, Mar. 1956, p. 49–55.

Takahashi et al "Recommended Practice for Small Punch (SP) Testing of Metallic Materials (Draft)", JAERI–M 88–172, Sep. 1988, p. 1–20.

John et al. "Yield Stress Determination by the Massachusetts Institute of Technology Miniaturized Bend Test", Nuclear Technology, vol. 92, Dec. 1990, p. 383–388.

Youngsuk et al. "A Plane Strain Punch Stretching Test for Evaluating Stamping Formability of Steel Sheets", Metallurgical and Materials Transactions A, vol. 25A, Oct. 1994, p. 2199–2205.

Foulds et al. "Small Punch Testing for Determining the Material Toughness of Low Alloy Steel Components in Service," Journal of Engineering Materials and Technology, vol. 116, p. 457–464, Oct. 1994.

Foulds et al. "Small Punch Testing for Irradiation Embrittlement," Materials Ageing and Component Life Extension, vol. I, V Bicego et al., eds. United Kingdom: Engineering Materials Advisory Services, Ltd., 1995, p. 273–284.

Muller et al. "An Analytical Feasability Study for Use of the Small Punch Test to Assess Integrity of Coated Structures," Materials Ageing and Component Life Estension, vol. I, V Bicego et al. eds., United Kingdom: Engineering Materials Advisory Services, Ltd., 1995, pp. 295–305.

* cited by examiner

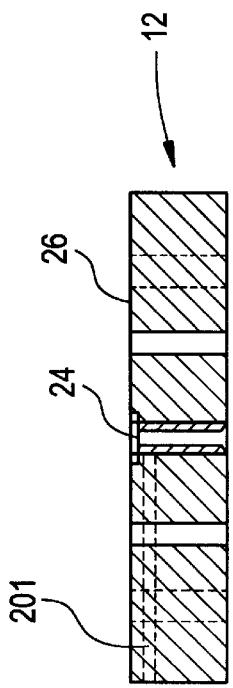
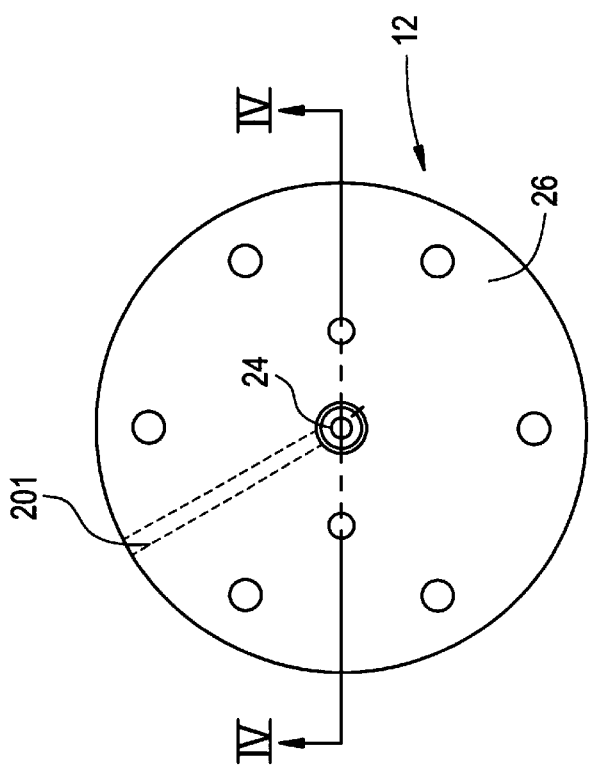
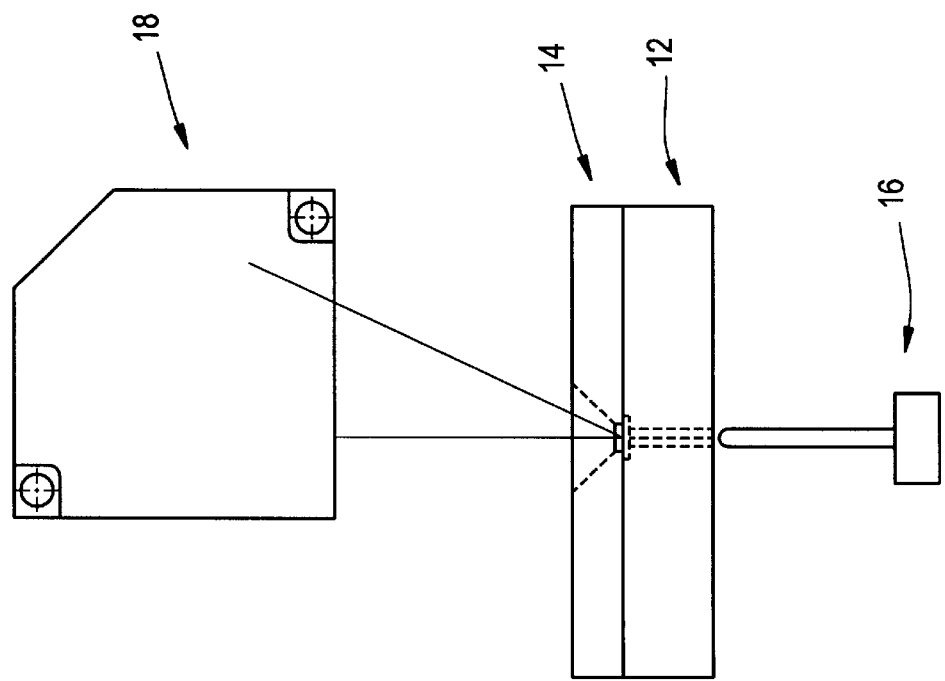

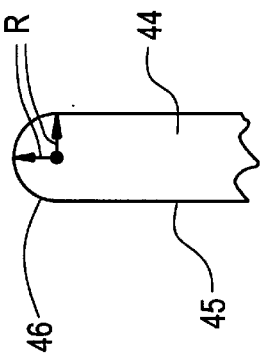
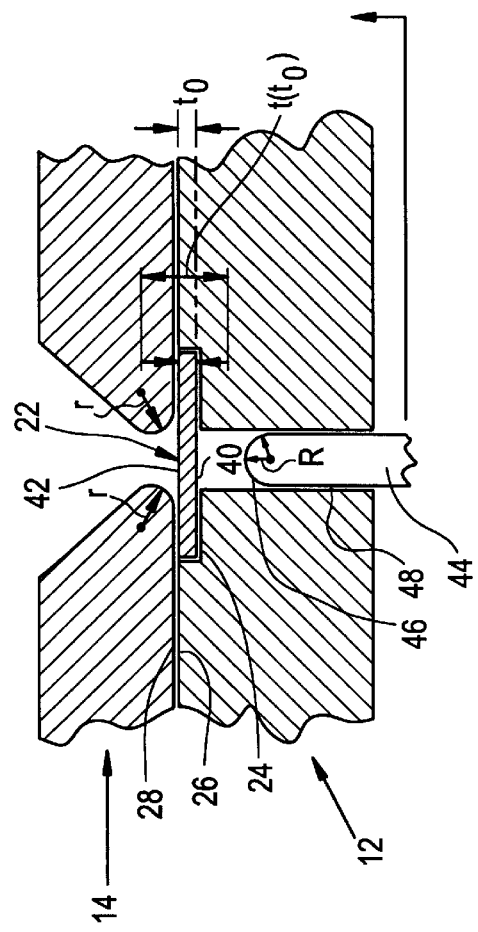
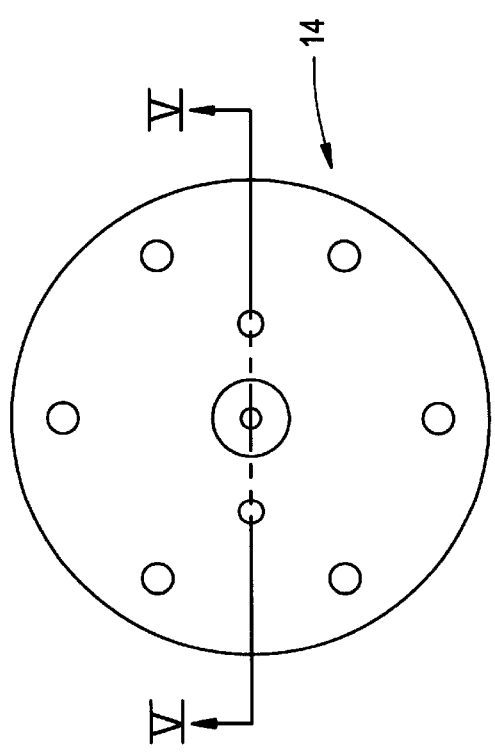
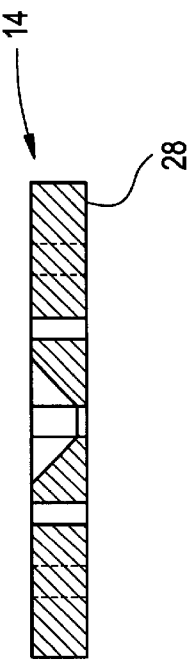

METHOD AND APPARATUS FOR DETERMINING THE TRUE STRESS AND TRUE STRAIN BEHAVIOR OF A DUCTILE POLYMER

FIELD OF THE INVENTION

This invention relates to the measurement of true stress and true strain behavior of ductile polymeric materials. More particularly, this invention relates to methods and apparatus for obtaining data regarding such behavior as the material goes through deformation and thereafter using such data to evaluate the material for use in human joint implants (e.g. artificial knees, hips, etc.).

BACKGROUND OF THE INVENTION

Before placing an artificial implant into a human or animal body the implant must be sterilized. The material, furthermore, must not only be biocompatible, but have as long a life as is feasible after sterilization. The importance of this latter characteristic, i.e. useful life expectancy, is accentuated when the implant is a load-bearing one, such as a total joint arthroplasty (e.g. a hip or knee).

For many years, polyethylene, and in particular, ultra high molecular weight polyethylene (UHMWPE), has been used for this purpose. Sterilization is accomplished in at least one of several ways. One known way was to irradiate the implant (e.g. joint replacement) with a gamma ray dose of 2.5–4.0 Mrads in the presence of air. While highly effective as a sterilization technique, it was known to result, at times, in the formation of free radicals in the polyethylene which combined with oxygen to eventually degrade the polymer and thus reduce its effective useful life. Such degradation, it has been found, not only occurs during shelf storage but, unfortunately, can also continue to occur after implantation in the body.

As a result of this undesirable degradation, gamma sterilization in air is generally no longer used in most UHMWPE implant situations, and other alternatives have been devised. For example, low oxygen environment gamma irradiation, ethylene oxide, and gas plasma sterilization are currently more often used. Unfortunately, it is yet to be clearly ascertained to what extent these new sterilization methods either inhibit or cause mechanical degradation of the polyethylene during shelf storage and/or after implantation in the body.

There are two particular times at which the testing of an implant to determine its "degradation" characteristic (or susceptibility) normally occurs. The first, of course, is before implantation. The next is if the implant is removed for failure or is suspected of being near failure. Ascertaining the true cause of failure aids future improvements. Moreover, being able to predict in vivo wear behavior in advance would obviously materially aid the technology and patients, alike.

It was known prior to this invention that meaningful comparative mechanical behavior data could be obtained for analyzing polyethylene implants by deriving and comparing load vs. displacement curves using small sample punch test techniques on material of a known polyethylene "standard" (i.e. nondegraded) implant and on material of an implant suspected of having experienced degradation or being tested for use, failure, or potential degradation. While such techniques are very useful, they do not measure true stress and corresponding true strain which, if capable of measurement, would give a more accurate indication of levels of degradation due to the changes which a ductile polymeric material, such as UHMWPE, goes through during multiaxial (e.g. biaxial) deformation.

While various physical and chemical properties of polyethylene can be readily measured by well known techniques, it is only recently that techniques for performing measurements of mechanical behavior on localized sections of such a material have been developed. For example, uniaxial tensile testing of 200–400 $\mu$m thick sections prepared from acetabular components have been utilized to investigate changes in mechanical behavior of the material in heavily oxidized subsurface regions, including local oxidation in total knee replacements. Yet another study prepared miniature tensile specimens from tibial components to compare mechanical properties of implants sterilized with ethylene oxide and gamma radiation. Unfortunately, the highly curved surfaces of total joint replacement components makes the fabrication of numerous long, flat uniaxial tensile specimens from a single implant technically impractical, and sometimes unfeasible.

Miniature specimen small punch testing techniques have heretofore been developed for measuring mechanical behavior of metals. Such known techniques have, in fact, been used successfully to characterize the true stress—true strain behavior, as well as the ductility and fracture resistance of metals. This development of the small punch test for metallic materials was driven by the need to measure in-service degradation of mechanical properties of metals with a limited volume of available material. The small specimen sizes (e.g. 0.02 inches thick) required for the test also provided a useful method for characterizing the material at specific locations in a component or a structure.

Certain researchers have heretofore empirically correlated the results of small punch mechanical behavior with conventional, relatively large test specimen mechanical behavior in metals. A major disadvantage of this empirical approach is the need to accumulate a large volume of mechanical (e.g. tensile and fracture) data for a given material in order to make reliable engineering predictions from small punch test results.

A known nonempirical alternative interpretation of the results of the small punch test data accumulated during the testing of metals is disclosed in U.S. Pat. No. 4,567,774. The technique reported uses the finite element method, or FEM, to infer conventional tensile stress-strain properties. Another known nonempirical technique matches the observed small punch load-displacement curve of the metal under analysis with a database of experimental and analytically simulated small punch load-displacement curves. From such a comparison, tensile stress-strain behavior in that metal can be inferred (i.e. an inferred true stress vs. true strain curve can be obtained). Such a stress/strain curve has been used to compute the local strain energy density accumulated to initiate cracking (i.e. fracture property) in the small punch metal specimen. Tensile and fracture properties using this known approach have been reasonably accurate for a wide range of metals. However, due to limitations in the constitute theory in these various nonempirical alternatives, they do not provide satisfactory results when applied to polymers such as polyethylene.

In this respect, the von Mises yielding criterion, which has been incorporated into the finite element models when nonempirical techniques have been employed, has been validated for metals. However, the theory has significant limitations with polymers generally, and with polyethylene specifically. For example, when applied to large-scale deformation mechanical behavior under multiaxial loading conditions when polymers stretch significantly, the von Mises yielding criterion no longer applies. Thus, these methods do not produce reliable estimates of the large-scale mechanical behavior of polymers under multiaxial loading conditions during the drawing (i.e. stretching) phase, which may often be of particular interest for the particular polymer under investigation. "Large-scale mechanical behavior" is defined (and known) as the behavior of a body under conditions wherein strains experienced are plastic over much of the body's volume (i.e. the "stretching" or "drawing" phase). In short, the known finite element based methods have not been found useful in reliably measuring or predicting stress/strain behavior for ductile polymers during the "stretching" phase. This is particularly true for polyethylene during the multi-axial loading conditions produced during and by a small punch test.

Despite the above drawbacks, the load-displacement behavior obtained by the known small punch testing methods for polymers, in general, and for polyethylene, in particular, has provided some useful results. In such tests, the punch head is caused to interact with the polymeric specimen at a constant displacement rate for the duration of the test. By gathering data and creating a "punch load vs. displacement curve" resulting from such a test on a particular material, the curve generated displays certain distinctive features, including an initial bending phase followed by a membrane drawing or stretching phase. In contrast, when metals are tested, virtually the entire test preceding the initiation of failure (cracking) consists of the bending phase with little or no stretching taking place. Thus, while load vs. displacement curves are highly useful for comparative analysis of metals, they are less satisfactory for use when comparing ductile polymers where failure initiates well after stretching has begun. In ductile polymers, their characteristics may differ markedly in the drawing phase, which characteristics are then not manifested in the load vs. displacement curves. Since in vivo implants may often be subjected, at least on their articulating surfaces, to multidirectional forces which create "drawing" or "stretching", it is important for a more accurate comparative analysis to generate curves which manifest the behavior of the polymer under "drawing" or "stretching" conditions. It has been left to this invention to achieve this more accurate result, as discussed below.

In this respect, and by way of a more detailed description, prior to our invention the mechanical behavior of polyethylene during the above-described small punch test has been empirically characterized from the load-displacement curve by measuring the initial peak load, the ultimate load, the ultimate displacement, and the work to failure (i.e., the area under the load-displacement curve). The small punch test has thus been used to characterize the load-displacement mechanical behavior of polyethylene with an uncertainty, in some instances, of less than 5%. Comparative analysis of a load-displacement curve obtained from a small punch test on a given material has then been compared with a curve similarly obtained for a known "standard" or "reference" material. Such a comparison has then been used to determine the acceptability of the material under test by subjectively comparing the shape of the load vs. displacement curve generated with that of the known "standard" material. Marked differences in the two curves resulted in rejection of the tested material. Absent from the comparison as stated above was a comparative analysis of the stress-strain behavior of either the "standard" material or the test material as it went through its stretching phase.

Despite the reproducibility and utility of such tests and of the load-displacement curves obtained, therefore, such results from this small punch testing are not completely satisfactory. For example, it has been observed that during the drawing phase of the test, a polyethylene specimen undergoes strain hardening or strain softening, depending upon the processing history and crosslink density of the polymer. Consequently, the load-displacement curves heretofore obtained do not permit a full analysis of the true stress-strain behavior of a ductile polymer, such as polyethylene, as would otherwise be desirable to know, particularly for assessing degradation or crosslinking in human implants.

It is thus apparent from the above that the prior art testing systems and procedures have not been able to fully characterize the large deformation mechanical behavior of ductile polymers in equibiaxial tension and, in this respect, have been unable to measure and generate complete true stress-true strain curves for comparative or other useful analytical purposes, particularly, but not necessarily limited to, ductile polymeric materials used in human (or animal) implants.

As used herein the term "true strain" ($\epsilon$) is defined as:

$$\epsilon = \ln(t_o/t) \tag{1}$$

wherein $t_o$ is the initial thickness of the sample of the material being tested; t is the instantaneous thickness of the material at any point in time, and at the location where true strain is being measured during punch test deformation, including up to catastrophic failure; and in is the natural logarithm.

As further used herein, the term "true stress" ($\sigma$) is defined as:

$$\sigma = \frac{P}{2\pi Rt + \pi t^2} \tag{2}$$

wherein P is the applied load; R is the radius of the hemispherical punch head used in the punch test; and t is the thickness of the sample being tested at any instant in time, including up to catastrophic breakage (failure). In certain embodiments the factor $\pi t^2$ is so small compared to the factor $2\pi Rt$, as to be properly considered negligible and thus may be ignored (i.e. not calculated) without significant loss of accuracy.

By the use of these two formulae in combination with certain unique method steps and apparatus, true stress/strain data may now be readily generated for ductile polymeric materials throughout the deformation of the material up to failure, thereby generating data which better reflects the mechanical changes in such polymeric material which occur when the polymer is deformed. From such data then, more meaningful comparative analyses can be done, particularly with respect to analyzing useful life and failure mode characteristics in various pieces of equipment made of such materials including, of course, human and animal implants, and other known areas where shelf life, etc., are important factors to assess and/or to predict.

In this respect, it is to be understood that this invention's utility is not necessarily restricted to human or other animal implants, to polyethylene polymers, nor to assessing failures after the implants have been removed. To the contrary, it is envisioned by this invention that "in situ" sampling is and may become feasible in the future. Due to the relatively small size of the sample needed in the tests herein used, it is quite conceivable that a sample may be taken of a particular polymeric product while still in situ in its intended environment (e.g. while still implanted or, if an industrial product, while still located in the machine in which it is functioning). Moreover, as new polymers are developed or old ones find new uses, this invention will become equally applicable to them.

From the above, it is apparent that there exists a need in the art for a new technology which can measure true stress and true strain in a ductile polymeric material under deformation and from such measurements gather data which can be used to do numerous useful things including assessing for acceptability and/or cause of failure in sterilized polymeric implants. It is a purpose of this invention to fulfill this and other needs which will become more apparent to the skilled artisan once given the following disclosure.

SUMMARY OF THE INVENTION

Generally speaking, this invention fulfills the above needs in the art by providing a method for measuring the true stress and true strain of a ductile polymeric material during deformation, the steps comprising:

a) providing a ductile polymeric material specimen having a generally planar shape defining substantially parallel first and second spaced planar surfaces having an initial substantially uniform thickness ($t_o$) therebetween;

b) providing a punch system which includes a movable punch head comprised of a first substantially hemispherical end having a predetermined radius (R) and means for mounting the specimen in engagable alignment with the first end of the punch head;

c) mounting the specimen in engagable alignment with the punch head;

d) engaging a planar surface of the specimen with the first end of the punch head;

e) substantially equibiaxially deforming the specimen with the punch head;

f) determining the thickness of the specimen during the deformation of the specimen by the punch head;

g) determining the load applied by the punch head during the deformation of the specimen; and h) determining the true stress and true strain of the specimen at at least one point in time during the deformation, according to the following formulae:

$$\text{true stress} = \frac{P}{2\pi Rt + \pi t^2} \quad (1)$$

$$\text{true strain} = \ln(t_o/t) \quad (2)$$

wherein P is the load applied; $t_o$ is the initial thickness of the specimen; t is the thickness of the specimen at the point in time of the determination during deformation; R is the radius of the punch head; and ln is the natural logarithm.

In certain embodiments the factor $\pi t^2$ is negligible compared to the factor $2\pi Rt$ and is thus not a part of the determination (i.e. it is ignored and not calculated) such that true stress is determined by the formula:

$$\frac{P}{2\pi Rt}$$

In certain further embodiments the determination of true stress and true strain is determined at a plurality of points in time throughout at least a portion of the deformation, and usually throughout the entire deformation cycle up to failure, so as to be sure to capture the full range of characteristics as it goes through its drawing phase during which the polymer may go through strain hardening, etc. This data may then be used to generate a characteristic true stress vs. true strain curve (i.e. an effective true stress vs. effective true strain curve) of the particular polymer being investigated. Such a curve, of course, will now reflect any strain hardening or softening which the polymer may have developed during deformation. Moreover, such a curve can be used, for example, to compare with a similarly derived curve of another sample (specimen) allegedly of the same polymer, but known to be an acceptable material (e.g. having an acceptable useful life after sterilization, for use in a human body implant). In this respect, both curves are normally to be derived by deforming the two specimens under similar conditions, such as at the same temperature and, preferably, as will be described more fully hereinbelow, at the same constant strain rate as well.

In certain preferred embodiments thickness measurements are taken at or near the punch center, i.e. the axis of symmetry of the hemispherical head of the punch.

In this respect, this invention also fulfills further needs in the art by providing a small punch test apparatus capable of performing specimen deformation at a substantially constant strain rate. Generally speaking, such an apparatus comprises in a small punch test apparatus including a punch head, means for mounting a substantially planar specimen in a position to be deformed by relative movement between the punch head and the mounting means, means for causing the punch head to deform the specimen and means for measuring a plurality of thicknesses of the specimen during deformation, the improvement comprising:

a) means for calculating the true strain of the specimen during deformation using the thickness as measured according to the formula:

$$\text{true strain} = \ln(t_o/t)$$

wherein $t_o$ is the initial thickness of the specimen; t is the measured thickness of the specimen; and ln is the natural logarithm; and b) means for controlling the relative movement between the punch head and the mounting means to achieve a constant strain rate during deformation in response to the calculation of the strain rate.

While the preferred embodiments of this invention and formula (1) above assume that the end of the punch head which contacts the specimen to deform it is a hemisphere of radius R, the skilled artisan will understand that other shapes, such as a solid ellipse, may be equivalently employed and formula (1) above adjusted accordingly such that deformation other than equibiaxial may be employed. In this respect, the term "equibiaxial deformation" is a term well understood in the art, and is used herein according to its well known meaning, and that other deformations are considered an equivalent, although a less preferred equivalent thereof.

This invention will now be described by reference to certain embodiments as illustrated in the following drawings.

BRIEF DESCRIPTION OF THE DRAWINGS

FIG. 2 is a side elevation view of the testing system depicted in FIG. 1 with portions removed;

FIG. 3 is a top plan view of a punch guide;

FIG. 4 is a cross-sectional view of the punch guide taken along line IV—IV of FIG. 3;

FIG. 5 is a top plan view of a punch die for the small punch testing system of the present invention;

FIG. 6 is a cross-sectional view of the punch die taken along line V—V of FIG. 5;

FIG. 7 is a side elevation view, partly in section of the punch guide and punch die prior to engaging a specimen in accordance with the present invention;

FIGS. 8A and 8B are partial views (side and top, respectively) demonstrating the hemispherical shape of the first end of an embodiment of a punch head contemplated by this invention;

DESCRIPTION OF CERTAIN EMBODIMENTS

One of the important features of certain embodiments of this invention is the ability of the method and apparatus employed to analyze a ductile polymer specimen during its substantially equibiaxial deformation up to failure, and particularly during that period of deformation when strain hardening may occur. The techniques of this invention are generally applicable to a wide variety of ductile polymers such as homopolymers and copolymers of polyethylene, polypropylene, polytetrafluoroethylene, as well as composite ductile materials which include one or more of these polymers. In this respect, this invention finds particular utility when used to analyze ultra high molecular weight polyethylene due to its prolific use in orthopaedic implants and the importance, therefore, of the need to know and predict their mechanical characteristics, particularly during in vivo loading (i.e. such as in a knee or hip replacement).

Figure 9:
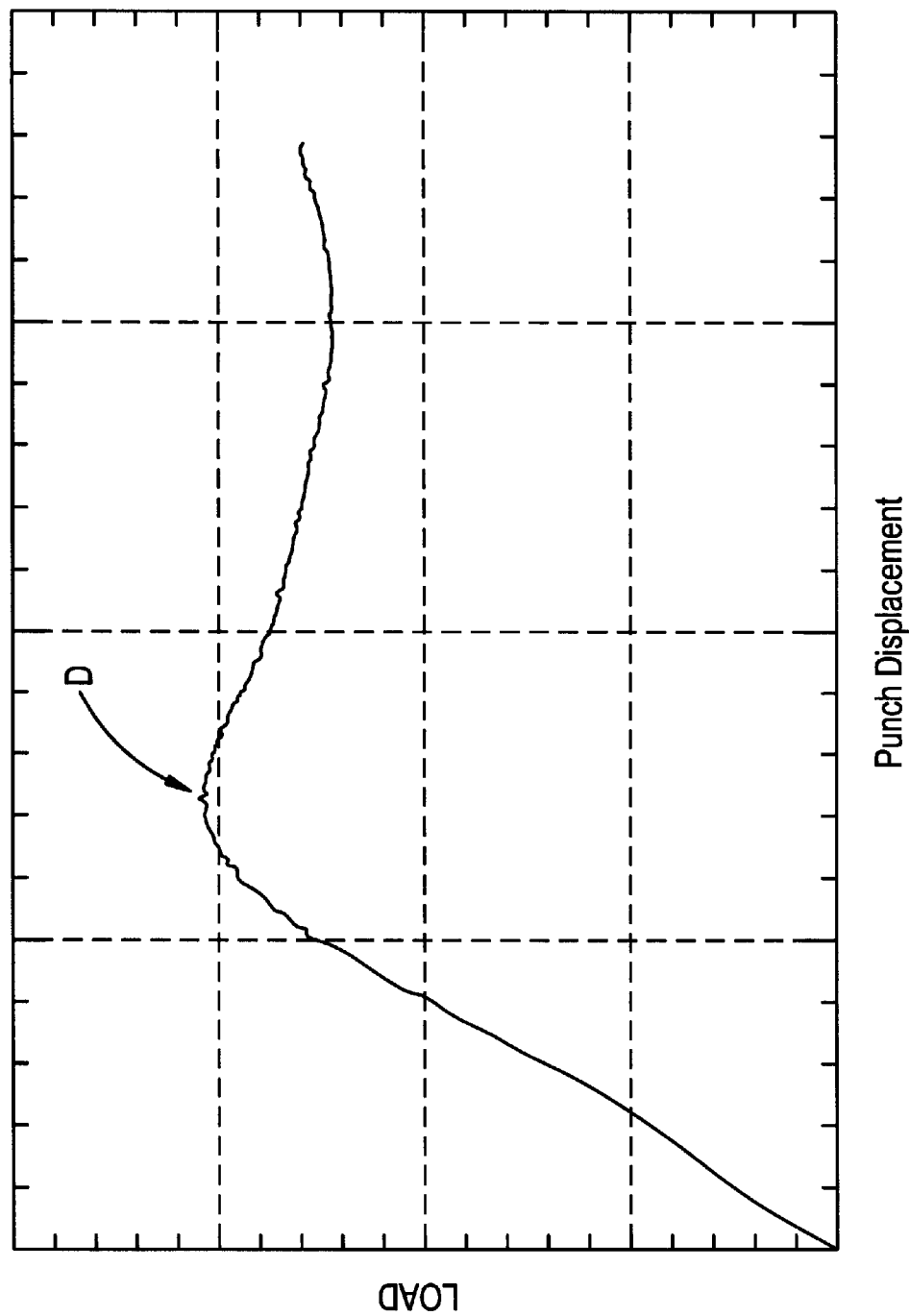
FIG. 9 is a load vs. punch displacement curve.
Figure 9A:
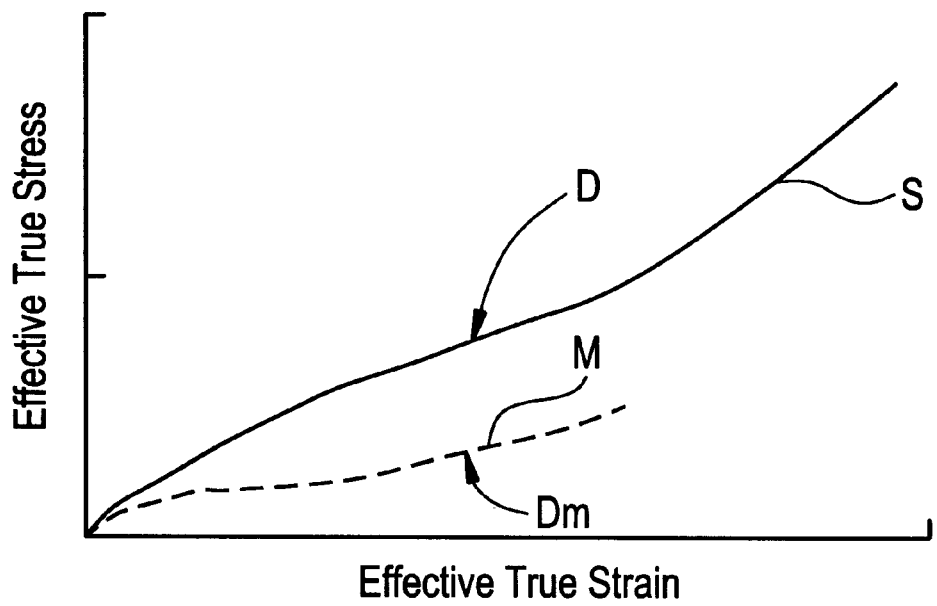
FIG. 9A are comparative stress vs. strain curves generated in the practice of certain methods and apparatus according to this invention.
Figure 10:
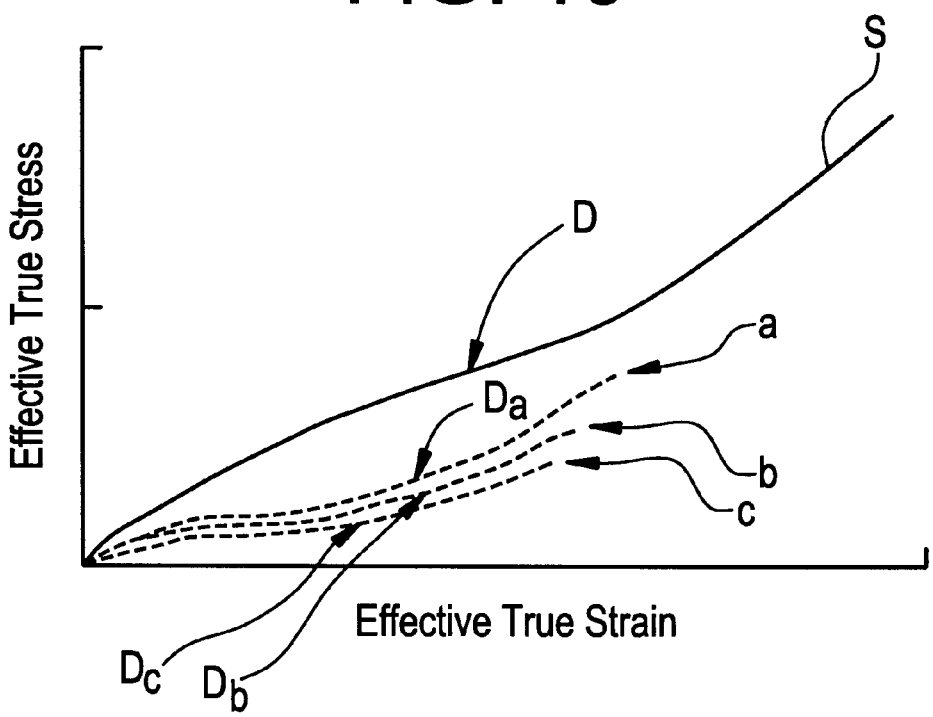
FIG. 10 are further comparative stress vs. strain curves generated in the practice of certain methods and apparatus according to this invention.

The methods of this invention will become more apparent to the skilled artisan from the following description of the apparatus illustrated in the drawings and a description of its operation, along with specific examples thereof whose curves are illustrated in FIGS. 9, 9A and 10.

Figure 1:
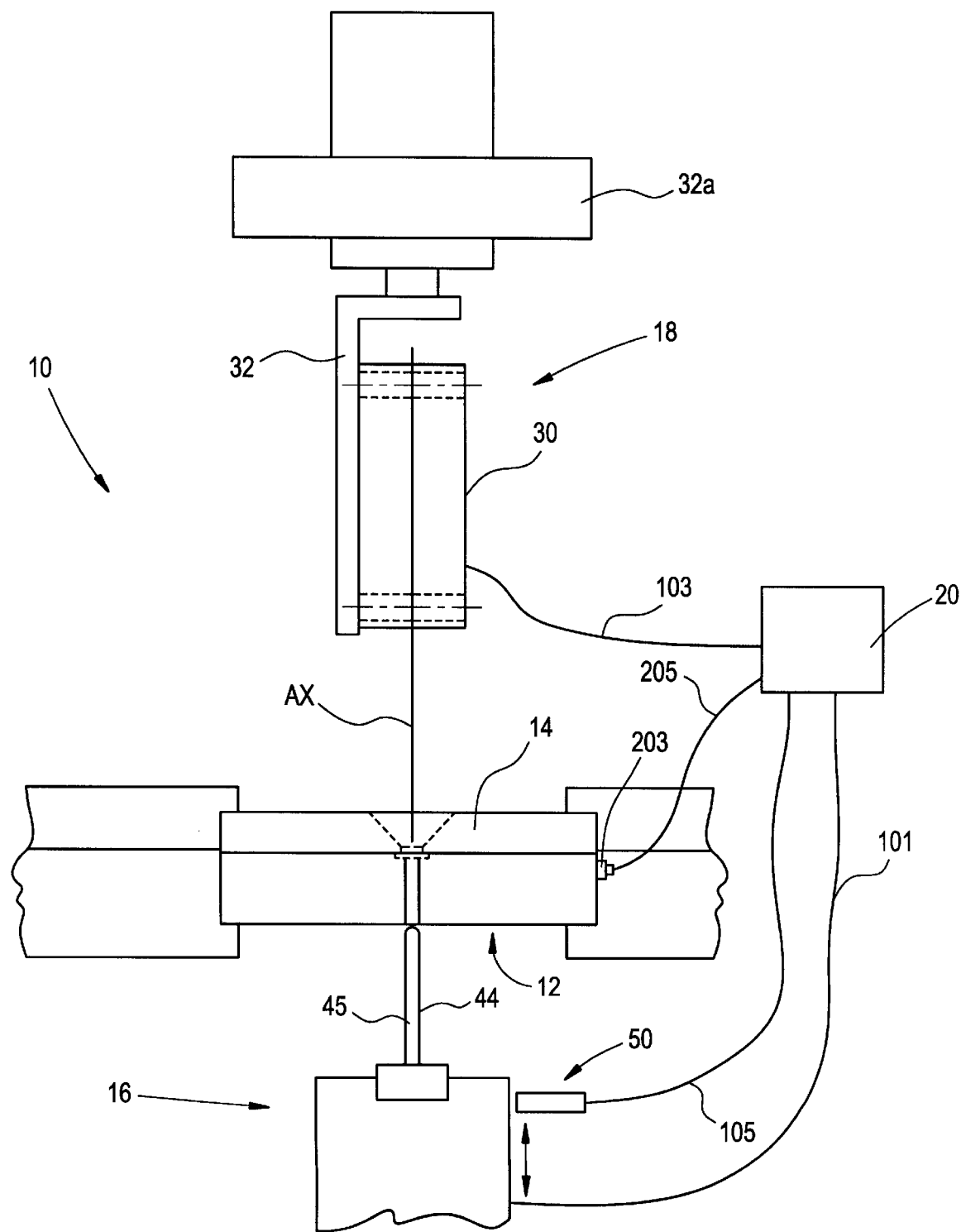
FIG. 1 is a schematic front elevation view of a first embodiment of a small punch testing system in accordance with the present invention.

Referring initially to FIG. 1, there is illustrated generally at 10 one embodiment of a small punch testing system for the measurement of true stress and true strain of polymers as contemplated by this invention. Testing system 10 is comprised of a punch guide, generally at 12, which includes a punch die 14; a punch control assembly, generally at 16; a punch 44 (discussed more fully below); a remote displacement measurement system, generally at 18 and 50; and a punch displacement control system, generally at 20.

Figure 1A:
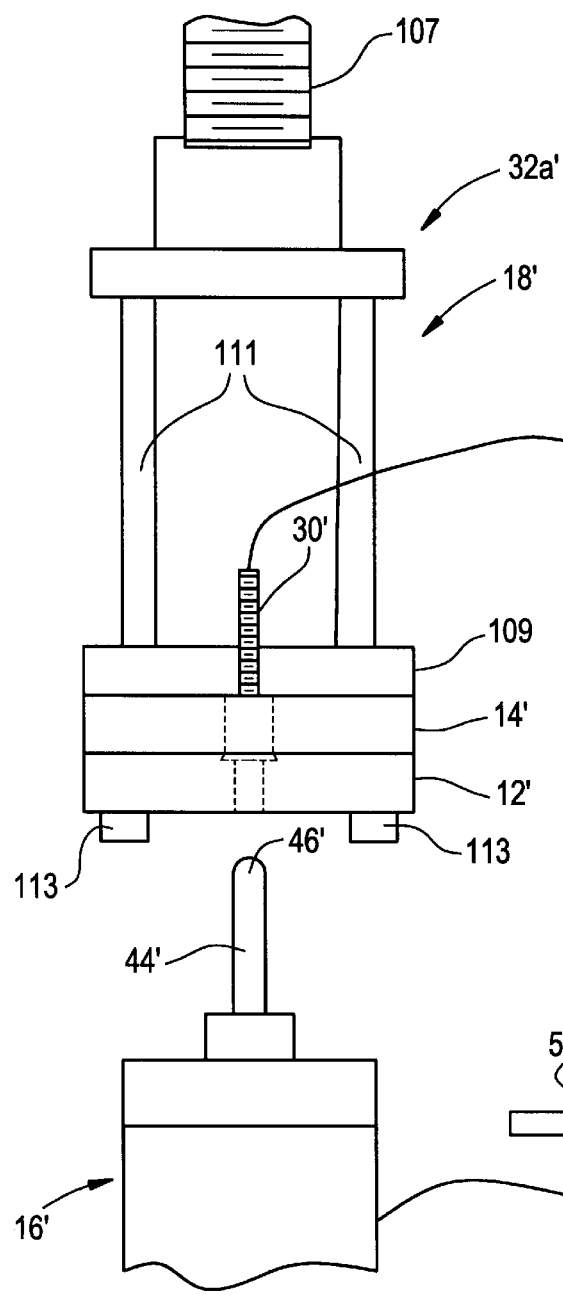
FIG. 1A is a schematic front elevational view of an apparatus similar to that of FIG. 1, but employing a different sensor.

Remote displacement measurement system 18 may be comprised of a laser sensor displacement measuring device 30 secured to laser sensor mounting bracket 32 that is, in turn, supported by a laser sensor holder 32a. The laser sensor displacement measuring device 30 may be any conventional, known commercially available device such as one available from Omron, Keyence, or other known manufacturers. Instead of a laser-type displacement measuring device, device 30 as illustrated in FIG. 1A, may also be an LVDT (linear variable differential transformer) such as a commercially available DVRT (differential variable reluctance transducer) which is commercially available from Mirco-Strain Inc. As will be described more fully below, device 30 (or 30') measures displacement of the top surface of the specimen at the axis of symmetry "AX" of the hemispherical head of the punch, while displacement device 50 measures punch 44's displacement. The difference is the change in thickness of the specimen at any instant in time.

Figure 1B:
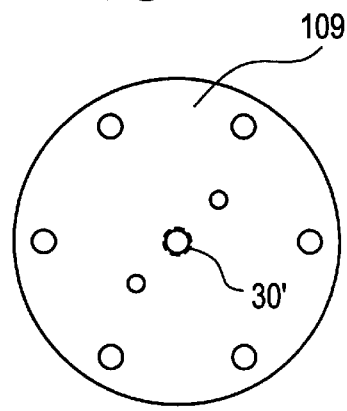
FIG. 1B is a top plan view of the DVRT or LVDT holder in FIG. 1A.
Figure 1C:
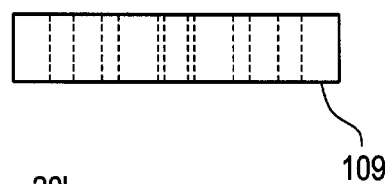
FIG. 1C is a side plan view of the DVRT or LVDT holder in FIG. 1B.

With reference more specifically to FIGS. 1A–C, the apparatus is essentially the same (with like apparatus being similarly numbered) except that laser sensor 30, and its holder 32, is replaced by LVDT sensor 30' and its accompanying holder apparatus. Punch 44' having hemispherical head 46' with a radius R and drive control assembly 16' are essentially the same as that illustrated in FIG. 1. Similarly, punch guide 12', punch die holder 32a', and punch die 14' are substantially similar to like items in FIG. 1 with only minor, conventional structural changes to 32a' and 14' as illustrated. In like manner, displacement control system 20' and punch displacement sensor 50' remain the same, accumulating and/or sending data via lines 101', 103', and 105'. Further illustrated is adjustable screw thread 107, LVDT holder plate assembly 109, and retaining columns 111 which are attached via cap screws 113. As illustrated in FIGS. 1B and 1C, plate 19 contains various orifices for accommodating sensor 30' and structural retaining elements such as columns 111.

With reference now more particularly to FIG. 7, there is illustrated a disc specimen 22 initially positioned in undeformed condition between punch guide 12 and punch die 14 where specimen 22 is retained in cooperatively shaped recess 24 formed in an upper surface 26 of punch guide 12. A face surface 28 of punch die 14 overlies punch guide face surface 26 and acts to hold specimen 22 in place in its cooperatively shaped recess 24. As can be seen, specimen 22 is a small disc, generally planar in shape, so as to define substantially parallel upper (42) and lower (40) surfaces separated by the thickness of the specimen "t" (or "$t_o$" before deformation).

As discussed above, the general apparatus shown in FIG. 7 has many similar features in common with U.S. Pat. No. 4,567,774 used for punch testing metals, as well as that as set forth in an article entitled "Fracture Toughness By Small Punch Testing" in the January 1995 publication, *Journal of Testing and Evaluation.* The principal differences in the inventive apparatus of this invention are discussed below. Generally speaking, however, the basic structure of holders and hemispherically domed punch heads for deforming specimens held in alignment with and to be deformed by such punch heads, is well known in the art and does not, by itself, constitute a part of our invention.

With reference particularly to FIGS. 8 and 8A, there is illustrated a preferred embodiment of the first end of the punch 44 for use in this invention. As illustrated, punch 44 includes a linearly extending cylindrical shaft portion 45 and a head 46 which is the end that contacts specimen 22 and creates the area of contact for deforming the specimen. As shown, punch head 46 is a true hemisphere, having a radius R (which is also the radius of cross-section of cylindrical shaft portion 45). Not only does the length of radius R thus become one of the factors in the above stress formula (a), but by specifying a true hemispherical shape, substantially equibiaxial deformation of the specimen is the result. In addition, die 14 is provided with a radius "r" at the end of its orifice contacting the specimen so as to prevent localized deformation of the specimen during the test.

In the practice of this invention where a material is under investigation for use in (or which has been used in) a body implant, miniature disc specimen 22 may be fabricated, for example, from a sample of a sterilized implant. A convenient size for the disc specimen is 0.5 mm (0.02 inches) in thickness and 6.4 mm (0.25 inches) in diameter. Specimens of other dimensions are, of course, usable. Each disc specimen when formed has, as aforesaid, a bottom or lower face 40 and a top or upper face 42.

As the punch 44 is caused to move (here, upwardly) through a central guide passage 48 in punch guide 12 (FIGS. 1 and 7), first hemispherical end 46 will engage the bottom or front—side surface 40 of the miniature disc specimen 22. Continued upward movement of the punch 44 will then initially cause specimen 22 to bow (bend) upwardly, and then, as further deformation occurs, to stretch and reduce thickness in a stretching (drawing) phase. Finally, further deformation will cause the specimen to rupture (i.e. fail). It can be seen from this description that by measuring stress and strain throughout all phases of deformation, and particularly in the stretching (i.e. drawing) phase up to failure, changes in mechanical characteristics (i.e. behavior), such as if the polymer undergoes strain hardening or strain softening, will be manifested in the stress-strain curve generated from the data collected.

For the purposes of making the calculations herein, generally, as well as including those embodiments where strain rate is to be maintained constant (discussed below), punch displacement control system 20 is constructed and is employed to do all calculations and to create signals to effect the required control of the apparatus, as well as to generate the data acquired from the calculations performed. Generally, the apparatus illustrated operates as follows:

A properly sized specimen 22 is mounted as shown in FIG. 7. Head 46 is then brought into initial contact with frontside surface 40 and the actual deformation is then begun by advancing punch 44 at a predetermined rate controlled by a conventional drive mechanism in control element 16 which may include, for example, a conventional, commercially available servohydraulic test frame and actuator (e.g. manufactured by MTS Corp., Eden Prairie, Minn.). Testing is conducted at a constant predetermined temperature, for example, at room temperature 20° C. (68° F.) or, if desired, at an average human body temperature (37° C. or 98.6° F.).

To maintain constant temperature and record it, punch guide 12 is provided with orifice 201 into which there is inserted a conventional thermocouple 203 (FIG. 1) which is connected via line 205 to control system 20. Control system 20 then monitors any temperature change and provides the necessary environmental response (not shown) to maintain the temperature substantially constant (e.g. ±2° C. or less).

Displacement of punch 44 is measured by a displacement measuring device 50, such as an extensometer manufactured by MTS Corp., Eden Prairie, Minn., and data acquired is sent to control assembly 20 via line 105. Control assembly 20 may, for example, include a conventional microprocessor loaded with data acquisition, data analysis, and conventional control software capable of computing and controlling the rate of movement of punch 44, and in certain embodiments as discussed below, for also computing instantaneously the strain rate during deformation and in response thereto varying the rate of movement of punch 44, if necessary, to maintain a constant true strain rate.

In addition to acquiring displacement data from device 50, control assembly 20 acquires data from laser or LVDT sensor measuring device 30 or 30' via line 103 (or 103') which senses movement in topside surface 42 of the specimen. Control 20, using the aforesaid microprocessor, then computes the instantaneous thickness at that given point in time at the axis of symmetry of the hemispherical head of the punch using the formula:

$$t = t_o - (d_p - d_b)$$

wherein t is the thickness of the specimen at that point in time and location sensed; to is the initial thickness before deformation; $d_p$ is the punch displacement sensed by device 50; and $d_b$ is the displacement of surface 42 as sensed by sensor 30 or 30'. Since all "variables" in formulae (1) and (2) above for computing the effective true stress and true strain are now known at that aforesaid particular point in time, control assembly 20 now calculates effective true stress and effective true strain for this specimen throughout any portion or all of the entire deformation cycle up to failure. From such data, then, curves, such as those shown in FIGS. 9–10, may be generated for comparative purposes as aforesaid.

For the most accurate comparison of two specimens, each test should be conducted as nearly as possible under the same conditions. This includes, in certain preferred embodiments, conducting each test at substantially the same constant strain rate. This is because the degree, if any, of strain hardening and/or strain softening which can occur in various ductile polymers (e.g. polyethylene) during the drawing phase of deformation is or may be dependent on the rate of strain. Thus, to insure a more accurate comparative analysis, strain rate should be maintained substantially constant.

A unique aspect of this invention is the providing of a small punch test apparatus which can achieve constant strain rate throughout deformation of the specimen. This is accomplished by control assembly 20 being adapted to include routinely designed software and feedback capabilities to the servohydraulic actuator in assembly 16 which controls the speed of punch 44 during deformation. Through the ability of this invention to calculate effective true strain in control assembly 20, acquisition of such data can then be used by assembly 20 (via line 101) to control the speed of punch 44 (and thus the change in thickness of specimen 22 ) to maintain the effective strain rate being calculated at a constant, often preselected, value. When such is accomplished and comparative curves are generated therefrom, a very good analysis can be made of the acceptability or unacceptability of a polymeric material intended for use in an implant (or other purpose) or in analyzing for failure mode if one has occurred (e.g. in an explant).

This invention will now be described with respect to certain examples thereof.

EXAMPLE 1

A disc-shaped specimen of ultra-high molecular weight polyethylene (UHMWPE) having a diameter of 0.250 inches and a thickness of 0.020 inches, is machined from stock material intended for use in the manufacture of a total joint replacement component. The specimen is placed in the device as illustrated schematically in FIG. 1A.

Control assembly 20' includes a conventional microprocessor loaded with data acquisition, data analysis, and control software capable of instantaneously computing and controlling the effective true strain rate of the specimen throughout deformation. This is accomplished by control assembly 20' sending a signal via line 101' to the servohydraulic actuator (not shown for convenience) in head control assembly extension 16' to control the advancement of punch 44' to effect a predetermined effective true rate of strain at 0.01 sec$^{-1}$ in the center of the specimen as contacted by the hemispherical head 46' of punch 44' having a radius of 0.05 inches (radius "r" of die 14 is 0.010 inches). The test is conducted and maintained at 20° C.±2° C. using the thermocouple control described above.

Initially operating in displacement control, the actuator is adjusted by the operator such that the head of the punch is placed in contact with the specimen retained in punch die 14'. The operator then changes from displacement control to strain control and starts the test. The control software in assembly 20' continuously acquires and computes the specimen thickness data being received from sensors 30' and 50' via lines 103' and 105', respectively, and computes thickness and effective instantaneous true strain therefrom. Any deviation from the present 0.01 sec$^{-1}$ rate of strain is then adjusted via line 101' which signals the appropriate adjustment in the rate of advancement of punch 44'.

During the test, load vs. displacement data is collected from the time of initial contact until failure of the specimen, and two curves are constructed. The first curve (FIG. 9) is load vs. displacement and the second curve (FIG. 9A) is effective true stress vs. effective true strain. The load vs. displacement curve is then used to determine the point "D", i.e. where the drawing or stretching phase began. This point is then located on the stress vs. strain curve to determine on this latter curve where the stretching phase began. This is accomplished by using the formulae (1) and (2) to correlate point D (FIG. 9) with stress and strain at that point on the stress/strain curve (FIG. 9A). Because this specimen is machined from an acceptable lot of UHMWPE suitable for use in a total joint replacement component, the stress/strain curve generated is designated as the reference standard for acceptable mechanical performance for future comparative analyses. This curve is shown in FIGS. 9A and 10 as the solid line curve marked "S".

With reference to FIG. 9, it can be seen that point "D" is located at the initial peak load where it begins to drop off. This point, in most situations, defines where the stretching of the polymer has begun to dominate. In some circumstances the beginning of the dominant stretching phase is not manifested by this drop off, but rather by some other significant change in the shape of the curve. In such circumstances, as experience will dictate to the skilled artisan, point D will be at this location.

EXAMPLE 2

A second lot of UHMWPE stock material, supposedly made of the same composition as the acceptable reference material of EXAMPLE 1, is now tested for evaluation to determine its acceptability or unacceptability under the same conditions as were used in conducting the test of EXAMPLE 1, namely:

A miniature disc-shaped specimen (0.250 inches in diameter and 0.020 inches in thickness) is machined from the second lot of UHMWPE and is tested using the same equipment as described in EXAMPLE 1 at 20° C.±2° C. and at a constant effective true strain rate of 0.01 sec$^{-1}$ which is maintained constant by the same procedure as in EXAMPLE 1. A second load vs. displacement curve (not shown) and another effective true stress vs. true strain curve are generated. This latter curve is then plotted as a dotted line marked ("M") in FIG. 9A and stretch initiation point Dm is located on the curve M for comparison with the standard "S" curve having its own point D. As illustrated, curve "M" differs markedly lower in stress and strain from curve "S", particularly beyond points D/Dm, and thus this new material is rejected as unacceptable for use as stock material for producing total joint replacement components.

EXAMPLE 3

In another test sequence whose stress-strain curves are illustrated in FIG. 10 (the load vs. displacement curves not being shown), a lot-controlled, sterilized UHMWPE total joint replacement component (knee) is retrieved from "shelf" inventory to determine if the mechanical behavior of the lot has degraded during the term of shelf storage.

The knee implant retrieved is placed in a milling machine and a standard coring tool is used to extract a core (approximately 0.275 inches in diameter) through the thickness of the implant. The central axis of the core is aligned perpendicular to the articulating surface of the implant. The core is then machined into three specimens labelled "a", "b", and "c", respectively. Each has a diameter of 0.250 inches and a thickness of 0.020 inches. The first specimen "a" is machined starting at a depth of 0.000 to 0.001 inches of the articulating surface to achieve a thickness of 0.020 inches. The second specimen "b" is machined at a depth from 0.060 and 0.080 inches from the surface. The third specimen "c" is machined at a depth from 0.100 and 0.120 inches from the surface.

All three specimens are tested using the conditions and apparatus as in EXAMPLE 1. The temperature is maintained at 20° C.±2° C. and the strain rate is controlled as described above, at a constant rate of strain of 0.01 sec$^{-1}$. Three effective true stress vs. true strain curves are generated (a, b, c, respectively, for like identified specimens) and plotted as illustrated in FIG. 10, along with the curve "S" for the standard generated in EXAMPLE 1 and stretch initiation points Da, Db, and Dc, respectively, are located thereon.

A comparison of the curves, particularly after points "D", demonstrates that the implant has substantially inferior subsurface stress and strain characteristics due probably to degradation during its shelf life. This implant is then rejected for use and others from the same lot with similar or older shelf life are either immediately rejected or further sample tested for possible degradation and unacceptability.

Once given the above disclosure many other features, modifications and improvements will become apparent to the skilled artisan. Such features, modifications and improvements are therefore considered a part of this invention, the scope of which is to be determined by the following claims:

We claim:

1. A method for measuring true stress and true strain of a ductile polymeric material during deformation, the steps comprising:

a) providing a ductile polymeric material specimen having a generally planar shape defining substantially parallel first and second spaced planar surfaces having an initial, substantially uniform thickness $t_o$ therebetween;

b) providing a punch system which includes a movable punch head comprised of a substantially hemispherical end having a predetermined radius (R) and means for mounting the specimen in engagable alignment with said end of the punch head;

c) mounting said specimen in engagable alignment with said punch head;
d) engaging a planar surface of said specimen with said first end of said punch head;
e) substantially equibiaxially deforming said specimen by applying a load thereto with said punch head;
f) determining a thickness of said specimen during said deformation of said specimen by said punch head;
g) determining said load applied by said punch head during said deformation of said specimen; and
h) determining said true stress and true strain of said specimen at at least one point in time of said deformation, according to the following formulae:

$$\text{true stress} = \frac{P}{2\pi Rt + \pi t^2} \quad (1)$$

$$\text{true strain} = \ln(t_o/t) \quad (2)$$

P is the load applied; $t_o$ is the initial thickness of the specimen; t is the thickness of the specimen at the point in time of said determination of said thickness during deformation; R is the radius of said punch head; and ln is the natural logarithm of the quantity $(t_o/t)$.

2. A method according to claim 1 which includes the step of omitting the calculation of the factor $\pi t^2$ in formula (1), during the step of determining said true stress and true strain and calculating the true stress according to the formula $P/2\pi Rt$.

3. A method according to claim 1 or 2 said steps of determining said thickness of said specimen and said load applied to said specimen during deformation comprises making said determinations at a plurality of thicknesses during deformation, and for each such thickness at which said determinations are made determining said true stress and true strain at such a thickness.

4. A method according to claim 3 which includes the further step of generating a curve of true stress versus true strain during deformation.

5. A method according to claim 4 which further includes repeating said method using another specimen and comparing said true stress and true strain curves as generated for the two specimens.

6. A method according to claim 4 which further includes the steps of generating a load/displacement curve for said specimen, determining from said load/displacement curve the point at which a stretching phase begins to dominate, locating on said curve of true stress versus true strain said point at which stretching begins to dominate, thereafter repeating said method using another specimen and comparing said true stress and true strain curves after said point at which stretching begins to dominate.

7. A method according to claim 1 or 2 such that said specimen consists essentially of polyethylene.

8. A method according to claim 1 or 2 such that said specimen is a portion of a material used in an artificial body implant.

9. A method according to claim 8 such that said artificial body implant is a human knee or hip implant and said material consists essentially of ultra high molecular weight polyethylene.

10. A method according to claim 5 such that said specimens are each a portion of a material used in an artificial body implant.

11. A method according to claim 10 such that said artificial body implant is a human knee or hip implant and said material consists essentially of ultra high molecular weight polyethylene.

12. A method for determining acceptability of a first ductile polymeric material, said method comprising the steps of:
a) selecting for use a quantity of a ductile polymeric material;
b) forming said material into a specimen having a generally planar shape defining substantially parallel first and second spaced planar surfaces having an initial substantially uniform thickness $(t_o)$ therebetween;
c) providing a punch system which includes a movable punch head substantially hemispherical in shape and having a predetermined hemispherical radius R and means for mounting said specimen in engagable relationship with said movable punch head;
d) mounting said specimen in said mounting means;
e) moving said punch head into engagement with said specimen;
f) continuing said movement of said punch head with respect to said specimen to apply a load to said specimen and to cause substantial deformation of said specimen;
g) determining said load applied by said punch head during said deformation;
h) determining a thickness of said specimen during said deformation;
i) calculating from said determinations acquired from steps g) and h) true stress and true strain of said specimen during said deformation according to the following formulae:

$$\text{true stress} = \frac{P}{2\pi Rt + \pi t^2} \quad (1)$$

$$\text{true strain} = \ln(t_o/t) \quad (2)$$

P is the said load applied; $t_o$ is the said initial thickness of the specimen; t is a said thickness of the specimen at a point in time of determination of said thickness during deformation; R is the said radius of said punch head; and ln is the natural logarithm of the quantity $(t_o/t)$; thereafter
j) comparing said true stress and true strain so calculated with said true stress and true strain of that of a second, acceptable ductile polymeric material comprised of substantially said same polymer providing said same method steps a)–i); and
k) using said comparison to determine acceptability of said first ductile polymer material from which said specimen is formed.

13. A method according to claim 12 such that said specimen consists essentially of high molecular weight polyethylene and said acceptable ductile polymeric material consists essentially of said same high molecular weight polyethylene as said specimen; said true stress and true strain of both said polymeric materials are determined by conducting steps at the same temperature and the said characteristic of acceptability is based upon the use of said polymeric materials in an artificial body implant.

14. A method according to claim 12 further including the steps of generating a load versus displacement curve for said specimen, determining a point on said load versus displacement curve where stretching begins to dominate, generating a true stress versus true strain curve of said specimen from said calculations of step i), locating said point on said true stress versus true strain curve of said specimen, generating similar curves for said acceptable ductile polymeric material and locating on said stress/strain curve for said acceptable polymer said point at which initial stretching dominates, and thereafter comparing said true stress versus said true strain curve of said specimen with that of said acceptable material after said initial point of stretching on said curves being compared.

15. A method according to claim 13 such that said deformations are conducted at a given constant rate of strain and said given constant rate of strain is the same for each material compared in step (j).

16. A method according to claim 13 such that said determination of said true stress and said true strain is made at a plurality of points in time during said deformation of said material compared and a curve of stress versus strain is generated for each said material compared from such a determination and said comparison includes a comparison of said curves.

17. A method according to claim 16 such that said deformations are conducted at a given constant rate of strain and said true stress and said true strain of said ductile polymeric materials are determined at the same said constant rate of strain and said curves include determinations made at points in time from the point of substantially initial punch head deformation until failure of said specimen.

18. A method according to claim 12 which further includes the steps of calculating at a plurality of points in time during said deformation of said specimen said true strain and adjusting said movement of said punch head with respect to said calculation to maintain said deformation at a constant rate of strain, and said deformation is substantially equibiaxial.

19. A method according to claim 1 which further includes the steps of moving said punch head with respect to said specimen to cause said deformation of said specimen.

20. A method according to claim 1 or 19 which further includes the steps of calculating at a plurality of points in time during deformation said true strain of said specimen and adjusting the rate of deformation of said specimen to maintain said deformation at a constant rate of strain.

21. In a small punch test apparatus including a punch head, means for mounting a substantially planar specimen in a position so as to be capable of being deformed by relative movement between said punch head and said mounting means, means for causing said punch head to deform said specimen and means for measuring a plurality of thicknesses of said specimen during deformation, the improvement comprising:

a) means for calculating true strain of said specimen during deformation using said thicknesses as measured according to the formula:

$$\text{true strain} = \ln(t_o/t)$$

wherein $t_o$ is an initial thickness of said specimen; t is a said measured thickness of the specimen; and ln is the natural logarithm of the quantity $(t_o/t)$; and b) means for controlling relative movement between said punch head and said mounting means to achieve a constant strain rate during deformation in response to said calculation of true strain.

22. In a small punch test apparatus according to claim 21 wherein said punch head includes an end for contacting said specimen, said end having a hemispherical shape such that relative movement of said punch head with respect to said specimen causes equibiaxial deformation of said specimen.

23. In a small punch test apparatus according to claim 21 or 22 wherein said means for mounting said specimen is stationary and said means for controlling the relative movement between said punch head and said specimen includes means for moving said punch head into deforming engagement with said specimen.

24. In a small punch test apparatus according to claim 23 wherein said calculating means further includes means for calculating the true stress of the specimen during deformation using the said thicknesses as measured, according to the formula:

$$\text{true stress} = \frac{P}{2\pi R t + \pi t^2}$$

wherein P is the load applied by the punch head; R is the radius of the hemisphere of said hemispherically shaped punch head; and t is the said measured thickness of the specimen.

* * * * *

UNITED STATES PATENT AND TRADEMARK OFFICE
CERTIFICATE OF CORRECTION

PATENT NO.    : 6,267,011 B1
DATED         : July 31, 2001
INVENTOR(S)   : Kurtz et al.

It is certified that error appears in the above-identified patent and that said Letters Patent is hereby corrected as shown below:

Column 2,
Line 54, delete "constitute" and insert -- constitutive --.

Signed and Sealed this

Tenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.     : 6,267,011 B1
DATED          : July 31, 2001
INVENTOR(S)    : Kurtz et al.

It is certified that error appears in the above-identified patent and that said Letters Patent is hereby corrected as shown below:

<u>Column 16,</u>
Line 30, delete "23" and insert -- 22 --.

Signed and Sealed this

Second Day of March, 2004

JON W. DUDAS
*Acting Director of the United States Patent and Trademark Office*